United States Patent [19]

Elbe et al.

[11] Patent Number: 4,739,119
[45] Date of Patent: Apr. 19, 1988

[54] PROCESS FOR THE PREPARATION OF HYDROXYBENZALDOXIME O-ETHERS

[75] Inventors: Hans-Ludwig Elbe; Reinhard Lantzsch, both of Wuppertal, Fed. Rep. of Germany

[73] Assignee: Bayer Aktiengesellschaft, Leverkusen, Fed. Rep. of Germany

[21] Appl. No.: 2,095

[22] Filed: Jan. 12, 1987

[30] Foreign Application Priority Data

Jan. 16, 1986 [DE] Fed. Rep. of Germany ....... 3601036

[51] Int. Cl.$^4$ ............................................. C07C 131/00
[52] U.S. Cl. .................................................... 564/256
[58] Field of Search ........................................ 564/256

[56] References Cited

PUBLICATIONS

Clark, N. G., *Modern Organic Chemistry*, (1964), Oxford Univ. Press., pp. 457–459.
Houben-Weyl, "Methoden der Organischen Chemie", vol. X/4, Stuttgart, Germany (1971), p. 268.

*Primary Examiner*—Donald B. Moyer
*Assistant Examiner*—L. Hendriksen
*Attorney, Agent, or Firm*—Sprung Horn Kramer & Woods

[57] ABSTRACT

A process for the preparation of a hydroxybenzaldoxime O-ether of the formula

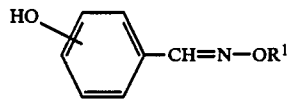

(I)

in which $R^1$ is alkyl, alkenyl or alkinyl, comprising reacting an aminobenzaldoxime O-ether of the formula

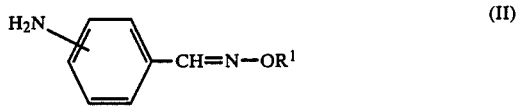

(II)

in which
$R^1$ has the abovementioned meaning,
with a diazotizing agent in acidic, aqueous solution, and thermally hydrolyzing the resulting diazonium salt of the formula

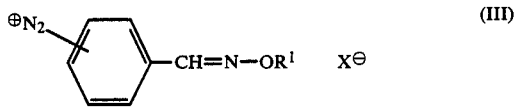

(III)

in which
$X^\ominus$ in an equivalent of an inorganic anion and
$R^1$ has the abovementioned meaning,
in acidic, aqueous solution without intermediate isolation.

The products are intermediates for agricultural and pharmaceutical chemicals.

Novel amino-benzaldoxime O-ethers of the formula

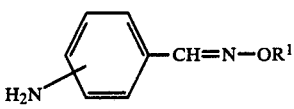

wherein $R^1$ has the above-mentioned meaning.

6 Claims, No Drawings

PROCESS FOR THE PREPARATION OF HYDROXYBENZALDOXIME O-ETHERS

The invention relates to a new process for the preparation of known hydroxybenzaldoxime O-ethers, which can be used as intermediates for the synthesis of compounds having fungicidal, insecticidal and antimycotic action.

It has already become known that certain hydroxybenzaldoxime O-ethers can be prepared by reacting hydroxybenzaldehydes with the appropriate hydroxylamine derivatives (cf. EP-OS (European published specification) No. 0,076,370 and EP-OS (European published specification) No. 0,115,828). The reaction concerned can be illustrated by the following equation:

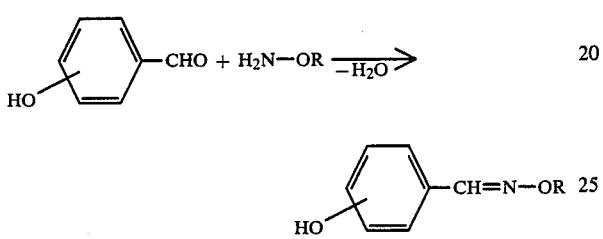

R=alkyl, alkenyl, alkinly.

However, the disadvantage of this process is that the starting materials are only accessible by a complicated synthesis. They are, therefore, relatively expensive and their use for the preparation of hydroxy-benzaldoxime O-ethers on a technical scale is problematic. Apart from this, the yields of hydroxy-benzaldoxime O-ethers using the abovementioned process are not always satisfactory.

It has now been found that known hydroxy-benzaldoxime O-ethers of the formula

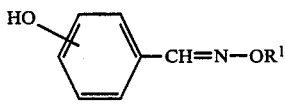

(I)

in which
R$^1$ represents alkyl, alkenyl or alkinyl,
are obtained when aminobenzaldoxime O-ethers of the formula

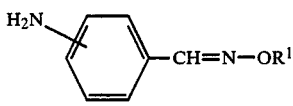

(II)

in which
R$^1$ has the abovementioned meaning,
are reacted with a diazotizing agent in acidic, aqueous solution, and the resulting diazonium salts of the formula

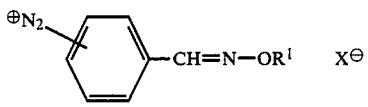

(III)

in which
X$^\ominus$ represents one equivalent of an inorganic anion and
R$^1$ has the abovementioned meaning,
are thermally hydrolyzed in acidic, aqueous solution without intermediate isolation.

It must be described as extremely surprising that the reaction according to the invention proceeds smoothly and in good yield under the stated process conditions, since it was not to be expected that the reactive carbocation (on the aromatic moiety) which arises during the thermal hydrolysis of the diazonium salt reacts selectively in the desired fashion and intermolecular attack on the free pair of electrons of the oxime ether nitrogen does not occur.

The process according to the invention is distinguished by a series of advantages. It allows the preparation of hydroxy-benzaldoxime O-ethers of the formula (I) in high yields, cheap and easily accessible compounds being employed as starting compounds. Furthermore, the reaction is simple to carry out and the isolation of the benzaldoxime O-ethers of the formula (I) presents no difficulties. The process according to the invention is, therefore, particularly suitable for preparation of hydroxybenzaldoxime O-ethers of the formula (I) on an industrial scale.

If, for example, 4-amino-benzaldoxime O-ethyl ether is used as starting material, aqueous sulphuric acid as acidic medium and sodium nitrite as diazotizing agent, then the course of the process according to the invention can be illustrated by the following reaction scheme:

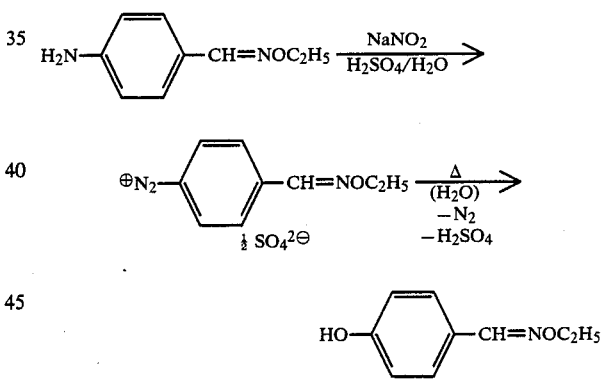

The amino-benzaldoxime O-ethers to be used as starting materials in the process according to the invention are generally defined by the formula (II). In this formula, R$^1$ preferably represents straight-chain or branched alkyl having 1 to 20 carbon atoms and also for, in each case, straight-chain or branched alkenyl and alkinyl having 3 to 20 carbon atoms in each base. The 4-amino-benzaldoxime O-ethers are here preferred in each case.

Particularly preferred starting materials are those aminobenzaldoxime O-ethers of the formula (II) in which R$^1$ represents straight-chain or branched alkyl having 1 to 10 carbon atoms and also in each case straight-chain or branched alkenyl and alkinyl having 3 to 10 carbon atoms in each case. The 4-amino-benzaldoxime O-ethers are here particularly preferred in each case.

Very particularly preferred starting materials are those 4-amino-benzaldoxime O-ethers of the formula (II) in which $R^1$ represents straight-chain or branched alkyl having 1 to 4 carbon atoms.

The amino-benzaldoxime O-ethers of the formula (II) are not yet known. They can be obtained by reacting amino-benzaldehydes of the formula

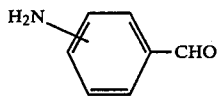  (IV)

with hydroxylamine O-ethers of the formula

  (V)

in which
$R^1$ has the abovementioned meaning,
or their hydrogen halide salts, in the presence of a polar, protic diluent and, if appropriate, in the presence of a base.

The following may preferably be mentioned as polar, protic diluent for the preparation of the aminobenzaldoxime O-ethers of the formula (II): alcohols, such as, for example, methanol, ethanol, n- and i-propanol and also n- and i-butanol; furthermore water and also glacial acetic acid.

The following may preferably be mentioned as bases for this process: sodium hydroxide, potassium hydroxide and sodium acetate.

The temperatures can be varied within a relatively wide range when the process for the preparation of aminobenzaldexime-O-ethers of the formula (II) is carried out. In general, the process is carried out at temperatures between 0° and 50° C., preferably between 10° and 30° C.

1 to 4 mols, preferably 1 to 2 mols, of hydroxylamine O-ethers of the formula (V), or their hydrogen halide salts, and, if appropriate, 1 to 4 mols, preferably 1 to 2 mols, of base are employed per mol of amino-benzaldehyde of the formula (IV) when this process is carried out. The reaction time is, in general, 5 to 15, preferably 5 to 10, hours. The amino-benzaldoxime O-ethers of the formula (II) are isolated in conventional fashion, such as, for example, by fractional distillation.

The amino-benzaldehydes of the formula (IV) are generally known compounds of organic chemistry (cf. Beilsteins Handbuch der Organischen Chemie [Beilstein's Handbook of Organic Chemistry], volume E III 14, p. 47, 53 and 57) or they can be obtained by the processes stated therein. 4-Amino-benzaldehyde is particularly preferred.

The hydroxylamino O-ethers of the formula (V) are likewise generally known compounds of organic chemistry (cf., for example, Houben-Weyl, Methoden der Organischen Chemie [Methods of Organic Chemistry], volume 10/1, p. 1181 et seq.) or they can be obtained by processes which are stated therein.

All components which are conventionally suitable for diazotization are suitable as diazotizing agent for the process according to the invention. Sodium nitrite, potassium nitrite, ammonium nitrite and nitrosylsulphuric acid are preferably among these.

The process according to the invention is carried out in acidic, aqueous solution. Suitable acids are preferably inorganic acids, such as, in particular, sulphuric acid.

The solutions here generally have a concentration of 1 to 50% by weight, preferably 1 to 30% by weight, of acid.

The temperatures can be varied within a relatively wide range when the process according to the invention is carried out.

The diazotization is generally carried out at temperatures between 0° and 20° C., preferably between 0° and 10° C.

The subsequent thermal hydrolysis of the diazonium salts is, in general, carried out at temperatures between 50° and 100° C., preferably between 70° and 100° C.

In general, 1 to 1.5 mol, preferably 1 to 1.2 mol, of diazotizing agent is employed per mol of aminobenzaldoxime O-ether of the formula (II) when the process according to the invention is carried out. The excess diazotizing agent can be destroyed in conventional fashion by addition of urea before the thermal hydrolysis.

In a preferred method for carrying out the process according to the invention, the diazonium salt solution is metered into aqueous sulphuric acid at 50° to 100° C., preferably 70° to 100° C., for thermal hydrolysis, the concentration of sulphuric acid being 1 to 50% by weight, preferably 1 to 30% by weight. The metering-in rate here is selected so that the temperature of the initially introduced aqueous sulphuric acid can be kept constant. The hydroxy-benzaldoxime O-ethers of the formula (I) are isolated in a generally known fashion (cf. also the preparation examples).

The hydroxy-benzaldoxime O-ethers of the formula (I) which can be prepared by the process according to the invention are generally useful starting materials for the synthesis of biologically active compounds. Thus, they can be used, for example for the synthesis of oxime ethers, which have good insecticidal properties (cf. EP-OS (European published specification) No. 0,115,828); of azolylphenoxy derivatives, which display excellent fungicidal properties (cf. EP-OS (European published specification) No. 0,076,370); of 1-hydroxyethyl-triazolyl derivatives which display good fungicidal and antimycotic properties (cf. EP-OS (European published specification) No. 0,110 048 and DE-OS (German published specification) No. 3,314,548); and also of hydroxyalkylazolyl derivatives, which have good antimycotic action (cf. DE-OS (German published specification) No. 3,427,844).

Thus, for example, 3,3-dimethyl-1-(4-methoximino-methyl-phenoxy)-1-(1,2,4-triazol-1-yl)-butan-2-one formula

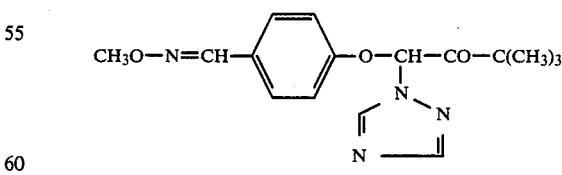

can be prepared by reacting 3,3-dimethyl-1-(1,2,4-triazol-1-yl)-butan-2-one initially with bromine to form 1-bromo(1,2,4-triazol-1-yl)-3,3-dimethyl-butan-2-one and subsequently reacting this with 4-hydroxybenzaldehyde O-methyloxime ether in the presence of a base. This synthesis can be illustrated by the formulae as follows:

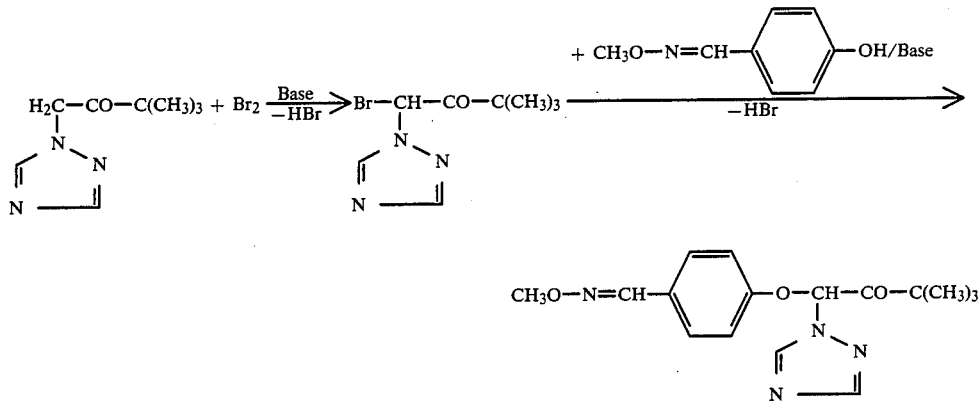

The process according to the invention is illustrated by the example below.

EXAMPLE 1

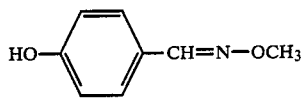
(I-I)

30 g (0.91 mol) of 4-methoximinometylaniline (content: 95.5%) are slurried in 120 g of 25% strength aqueous sulphuric acid. The slurry is stirred for 30 minutes at room temperature and then cooled to 5°–10° C. A solution of 13.8 g (0.2 mol) of sodium nitrite in 80 ml of water are allowed to drop into the reaction mixture within 30 minutes. The mixture is then stirred for 1 hour at 5°–10° C. and the excess nitrite is subsequently destroyed by added urea.

For hydrolysis, the diazonium solution is run, as rapidly as possible, into initially introduced aqueous sulphuric acid (120 g, 25% strength) at 80°–85° C., the temperature being kept constant. After completion of the addition, the mixture is stirred for 15 minutes at 80°–85° C. For work-up, the mixture is cooled to room temperature, adjusted to pH 5–6 using aqueous sodium hydroxide solution and extracted with methylene chloride. The organic phase is concentrated under reduced pressure. The crude product which remains is distilled in vacuo. 25.7 g (content according to GC: 95.4%; yield: 85% of theory) of 4-methoximinomethylphenol of boiling point 140°–142° C./0.13 mbar are obtained.

Preparation of the Starting Compound

H₂N—⟨benzene⟩—CH=N—OCH₃ (II-I)

170 g (0.98 mol) of 4-aminobenzaldehyde (moist, 70% strength) are dissolved in 1.5 l of methanol. The solution is treated with 300 ml of water, and 119.1 g (1.44 mol) of sodium acetate and 120 g (1.44 mol) of O-methylhydroxylamine are added to this. The mixture is stirred for 10 hours at room temperature and filtered off with suction from the inorganic residue, and the filtrate is concentrated under reduced pressure. 134.9 g (content according to GC: 95.5%; yield 88% of theory) of 4-methoximinomethylaniline of boiling point 110°–115° C./0.27 mbar are obtained.

Preparation of the Compound of the Formula

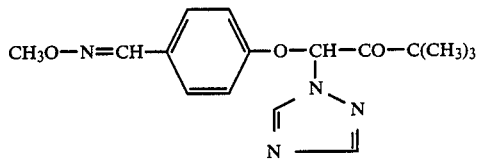

110 g (1.34 mol) of sodium acetate are introduced into a solution of 217 g (1.3 mol) of 3,3-dimethyl-1-(1, 2,4-triazol-1-yl)-2-butanone in 700 ml of glacial acetic acid, the temperature increasing to about 28° C. The mixture is stirred for 30 minutes and treated dropwise with 208 g (1.3 mol) of bromine, with slight cooling at 30 to 33° C. The reaction mixture is then stirred for 2.5 hours at room temperature and poured into 1200 ml of water. The reaction product is extracted with methylene chloride, washed with water and aqueous bicarbonate solution, dried over sodium sulphate and concentrated.

The crude 1-bromo-3,3-dimethyl-1-(1,2,4-triazol-1-yl)-2-butanone thus obtained is dissolved in 100 ml of acetonitrile and passed into a slurry of 151 g (1 mol) of 4-methoximinomethylphenol and 150 g (1.09 mol) of potassium carbonate in 800 ml of acetonitrile, the temperature increasing to about 40° C. The reaction mixture is stirred for 3 hours at 60 to 65° C., subsequently cooled and poured onto water. The reaction product is extracted with toluene, washed with water, dried and concentrated. The residue is triturated in ligroin and dried on clay. 241 g (76% of theory) of 3,3-dimethyl-1-(4-methoximinomethyl-phenoxy)-1-(1,2,4-triazol-1-yl)-butan-2-one of melting point 83°–87° C. are obtained.

It will be understood that the specification and examples are illustrative but not limitative of the present invention and that other embodiments within the spirit and scope of the invention will suggest themselves to those skilled in the art.

What is claimed is:

1. A process for the preparation of a hydroxy-brenzaldoxime O-ether of the formula

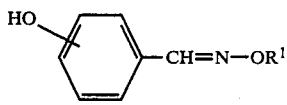

(I)

in which

R¹ is alkyl, alkenyl or alkinyl, comprising reacting an aminobenzaldoxime O-ether of the formula

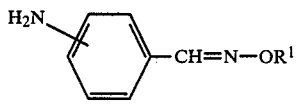

(II)

with a diazotizing agent in acidic, aqueous solution at a temperature between 0° and 20° C., and then without intermediate isolation thermally hydrolyzing the resulting diazonium salt of the formula

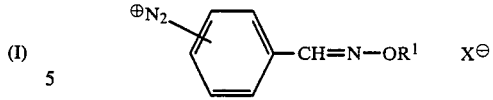

(III)

in which

X⊖ is an equivalent of an inorganic anion, in acidic, aqueous solution at a temperature between 50° and 100° C.

2. A process according to claim 1, wherein an aminobenzaldoxime O-ether is employed, in which
R¹ is straight-chain or branched alkyl having 1 to 20 carbon atoms, alkenyl having 3 to 20 carbon atoms or alkinyl having 3 to 20 carbon atoms.

3. A process according to claim 1, wherein an aminobenzaldoxime O-ether is employed, in which
R¹ is straight-chain or branched alkyl having 1 to 10 carbon atoms, alkenyl having 3 to 10 carbon atoms or alkinyl having 3 to 10 carbon atoms.

4. A process according to claim 1, wherein an aminobenzaldoxime O-ether is employed, in which R¹ is straight-chain or branched alkyl having 1 to 4 carbon atoms.

5. A process according to claim 1, wherein the diazotizing agent is a compound selected from sodium nitrite, potassium nitrite, ammonium nitrite and nitrosylsulphuric acid.

6. A process according to claim 1, wherein the acidifying agent is aqueous sulphuric acid.

* * * * *